United States Patent [19]

De Rosa et al.

[11] Patent Number: 5,538,955
[45] Date of Patent: Jul. 23, 1996

[54] PROCESS FOR THE PREPARATION OF IODINATED BIOPOLYMERS HAVING DISINFECTANT AND CICATRIZING ACTIVITY, AND THE IODINATED BIOPOLYMERS OBTAINABLE THEREBY

[75] Inventors: Alfredo De Rosa, Naples; Armando Rossi, Arco Felice; Pietro Affaitati, Rome, all of Italy

[73] Assignees: Development Biotechnological Processes S.N.C Di Pelliccia Maria Teresa, Avellino; IMS-International Medical Service SRL, Rome, both of Italy

[21] Appl. No.: 362,568
[22] PCT Filed: Apr. 28, 1994
[86] PCT No.: PCT/IT94/00052
    § 371 Date: Jan. 3, 1995
    § 102(e) Date: Jan. 3, 1995
[87] PCT Pub. No.: WO94/26788
    PCT Pub. Date: Nov. 24, 1994

[30] Foreign Application Priority Data

May 7, 1993 [IT] Italy ................. RM93A0291

[51] Int. Cl.⁶ ..................... C08B 37/08; A61K 31/70
[52] U.S. Cl. ..................... 514/55; 536/20; 536/124
[58] Field of Search ................. 536/20, 124; 514/55

[56] References Cited

U.S. PATENT DOCUMENTS

| | | | |
|---|---|---|---|
| 4,275,194 | 6/1981 | Kato et al. | 536/20 |
| 4,424,346 | 1/1984 | Hall et al. | 536/20 |
| 5,051,256 | 9/1991 | Barnes | 424/402 |
| 5,336,415 | 8/1994 | Deans | 210/725 |

FOREIGN PATENT DOCUMENTS 04178329  6/1992  Japan.

OTHER PUBLICATIONS

Journal Of The Applied Polymer Science. vol. 25, 1980, pp. 731–738. Y. Shigeno et al. "On the Adsorption of Iodine onto Chitosan".

Database WPI. Week 9232, Derwent Publications Ltd., London, GB; AN 263004 & JP, A, 4 178 329 (Unitika) 25 Jun. 1992. Patent Abstracts Of Japan. vol. 16, No. 485 (C–0993).

Takahashi *J. Inclusion Phenomena* 1987, 5, 525–534.

Shigeno et al. *Angew. Makromolecul. Chem.* 1980, 91, 55–67.

Primary Examiner—Gary L. Kunz
Assistant Examiner—Kathleen Kahler Fonda
Attorney, Agent, or Firm—Browdy and Neimark

[57] ABSTRACT

Process for the preparation of complexes of iodine with chitosan or derivatives thereof, and the iodinated compounds thus obtainable. Said compounds take form of powders, which may contain over 60% of iodine in its elementary form. In a dry state the iodine bound to the chitosan or derivatives thereof does not sublimate. If the percentage content of iodine does not exceed 50 % (by weight), said powders can be dissolved in aqueous solvents of an acid type, such as, for example, diluted acetic acid or glutamic acid. Said solutions are compatible with addition of surfactants, preferably of a non-ionic type, which improve the solubility of the chitosan-iodine complex. Solutions with identical characteristics can, alternatively, be prepared by solubilizing, heating if necessary the iodine in a suitable surfactant, preferably non-ionic, and adding this solution under rapid stirring to the chitosan derivatives thereof, dissolved in water, optionally in the presence of acids or salts. Alternatively, the chitosan or derivatives thereof in a dry state can be added to the solution of iodine in surfactant which rapidly absorbs onto the solid, forming the chitosan-iodine complexes. This material suspended in water or in acid solutions, preferably acetic acid or glutamic acid, solubilizes rapidly. The complexes of iodine with chitosan or derivatives thereof, in the form of aspersable powders, solutions or ointments, thanks to their disinfectant and cicatrizing properties, can be used in the field of surgery post-operative treatment and more generally speaking as products for topical use for medication of wounds and disinfection of the skin. Another area of interest in which the complexes can be used as an active principle is the field of cosmetics.

25 Claims, No Drawings

PROCESS FOR THE PREPARATION OF IODINATED BIOPOLYMERS HAVING DISINFECTANT AND CICATRIZING ACTIVITY, AND THE IODINATED BIOPOLYMERS OBTAINABLE THEREBY

DESCRIPTION

The present invention has as its subject a process for the preparation of complexes of iodine with chitosan or deacetylated, acylated with mono- or polycarboxylic acids, aldyminated, N or O-carboxymethylated or sulphatated derivatives thereof and their salts, the iodinated complexes thus obtainable and the therapeutical compounds containing them as an active principle.

According to a particularly preferred embodiment, the present invention has as its subject complexes of iodine with chitosan and derivatives thereof, containing iodine in a proportion expressed by the general formula $X(I_2)_n$, in which X is the monomeric unit of a polymer chosen from the group comprising chitin, chitosan, N-carboxybutylchitosan, N-acylchitosans, N-carboxymethylchitosan, N-O-carboxymethylchitosan, N-O-chitosan sulphate and n is a number variable from 0.01 to 1.5.

According to a still more particularly preferred embodiment, X is chosen from the group comprising the monomeric units given in the following Table 1.

TABLE 1

Meanings of X in the general formula $X(I_2)n$

| Polysaccharide^ | Type of monomeric unit° |
|---|---|
| Chitin | A B * |
| Chitosan | A B * |
| N-carboxybutyl chitosan | A B C |
| N-acylchitosans | A B D |
| N-carboxymethyl chitosan | A B E |
| N—O-carboxymethyl chitosan | A B E F |
| N-carboxymethyl chitosan | A B G |
| N—O-chitosan sulphate | A B H I |

(°) Monomeric units: 2-amino-2-deoxy-β-D-glycan
(A); 2-acetamido-2-deoxy-β-D-glycan
(B); 2-N-carboxybutylamino-2-deoxy-β-D-glycan
(C); 2-N-acylamino-2-deoxy-β-D-glycan in which acyl is for example propionyl, butyrryl, caproyl, oxalyl, succinyl, phtalyl etc.
(D); 2-N-carboxymethylamino-2-deoxy-β-D-glycan
(E); 2-N-carboxymethylamino-2-deoxy-β-D-6-O-carboxymethylglycan
(F); 2-N-dihydroxypropylamino-2-deoxy-β-D-glycan
(G); 2-amino-2-deoxy-β-D-glycan N-sulphate
(H); 2-amino-2-deoxy-β-D-glycan O-sulphate (I);
(*) In chitin the monomeric unit B prevails, whereas in chitosan the gradual increase of monomeric unit A imparts a growing water-solubility to the polymer in an acid environment.
(^) In the polymers given above, whose molecular weight may vary from several thousand to millions of Dalton, the monomeric units are bound together by glycosidic β 1–4 bonds. The ionizable groups, according to their pH, are salified by counterions of organic and inorganic nature.

Iodine in its elementary state exhibits notable germicidal activity, for this reason it is used in alcoholic solutions as a disinfectant for topical use.

The limits to said use are the low stability over a period of time of the iodine solutions, the notable aggressiveness of this halogen on the tissues when applied as a solution, and the persistent stains it leaves on the skin.

More recently, water-soluble forms of iodine with polyvinylpyrrolidone have been commercialized, which only partially mitigate these undesirable negative effects.

There is therefore great interest in the development of "slow release" iodine-based forms which allow application of large quantities of active principle, which are then released gradually but continually, so as to guarantee effective defence from infection by microorganisms over a long period, without damaging the tissues and reducing the number of medications required.

Of particularly great advantage is the possibility of coupling the iodine with compounds capable of stimulating tissue regeneration, so as to aid the healing process as a whole.

From this point of view chitin, chitosan and in general the other derivatives of this polysaccharide, only partially indicated in Table 1, are of particular interest according to the present invention, due to their notable cicatrizing and hemostatic powers.

Chitin, a biopolymer present in a large number of living organisms, such as arthropods, annelids, mollusks, coelenterates and fungi, is a polysaccharide with a molecular weight varying from a few thousand to several million Dalton, formed by molecules of 2-amino-2-deoxy-β-D-glycan and 2-acetamido-2-deoxy-β-D-glycan which are bound together, in a variable ratio, with glycosidic β1–4 bonds. In natural chitins over 70% of the monomeric units are in general formed by 2-acetamido-2-deoxy-β-D-glycan, giving the polymer a high level of insolubility in water. By controlled chemical hydrolysis of the acetamidic bond it is possible to obtain water soluble chitins, called chitosans, in which the 2-amino-2-deoxy-β-D-glycan, salified in various ways, is the prevalent monomeric unit.

A large amount of literature confirms the important cicatrizing and in particular hemostatic properties of chitosan and some of the derivatives thereof (K. Suzuki et al., Microbial. Immunol., 1984, 28, 903; K. Nishimura et al., in Chitin in Nature and Technology, Ch. Jeuniaux and G. W. Gooday esd., Plenum Press, N.Y., London, 1986, 477; K. Nishimura et al., J. Biomed. Mat. Res., 1986, 20, 1359; P. L. Sapelli et al., in Chitin in Nature and Technology, Ch. Jeuniaux and G. W. Gooday eds., Plenum Press, N.Y., London, 1986; G. Biagini et al., in Basic and Applied Hystochemistry, Soc. Ital. Istochim., Rome, 1987; J. Knapczyk et al., in Chitin and Chitosan, G. SkjakBraek, T. Anthonsen and P. Sandford eds., Elsevier 1989, 605; J. Knapczyk et al., in Chitin and Chitosan, G. Skjak-Braek, T. Anthonsen and P. Sandford eds., Elsevier 1989, 657; G. Biagini et al, in Chitin and Chitosan, G. Skjak-Braek, T. Anthonsen and P. Sandford eds., Elsevier 1989, 671; B. Lei and C. R. Wildevuur, Plast. Reconstr. Surg., 1989, 84, 960; R. Muzzarelli et al., Biomaterials, 1989, 10, 598; T. Chandi and C. P. Sharma, Biomater. Artif. Cells Artif. Organs, 1990, 18, 1; G.-hi. Kind et al., Curr. Surg. 1990, 47, 37; P. M. Santos et al., Otolaryngol. Head Neck Surg., 1991, 105, 12; G. Biagini et al., Biomaterials, 1991, 12, 287; G. Biagini et al., Biomaterials, 1991, 12, 281; P. R. Klokkevold et al., J. Oral Maxillofac. Surg., 1991, 49, 858), the ability of these polymeric matrixes to support cell growth (S. Miyazaki et al., Chem. Pharm. Bull., 1981, 29, 3067; S. K. Kim and C. Rha, in Chitin and Chitosan, G. Skjak-Braek, T. Anthonsen and P. Sandford eds., Elsevier 1989, 617; M. Izume et al., in Chitin and Chitosan, G. Skjak-Braek, T. Anthonsen and P. Sandford eds., Elsevier 1989, 653) and the possibility of using these biomolecules as systems for the controlled release of drugs and biomaterials for medical use (R. Muzzarelli, Carbohydrate Polymers, 1983, 3, 53; S. H. Pangburn et al., in Chitin and Chitosan Enzymes, J. P. Zikakis ed., Academic Press., N.Y. 1984, 3; Y. Kawashima et al., Chem. Pharm. Bull., 1985, 33, 2107; W. M. Hou, Chem. Pharm. Bull., 1985, 33, 3986; T. Nagai et al., in Chitin and Chitosan Enzymes, J. P. Zikakis ed., Academic Press., N.Y. 1984, 21; T. Dolan et al., in Chitin in Nature and Technology, Ch.

Jeuniaux and G. W. Gooday eds., Plenum Press, N.Y., London, 1986; R. Muzzarelli et al., Biomaterials, 1988, 9, 247; J. Knapczyk et al., in Chitin and Chitosan, G. Skjak-Braek, T. Anthonsen and P. Sandford eds., Elsevier 1989, 665; C. J. Brine, in Chitin and Chitosan, G. Skjak-Braek, T. Anthonsen and P. Sandford eds., Elsevier 1989, 679; Y. Machida et al., in Chitin and Chitosan, G. Skjak-Braek, T. Anthonsen and P. Sandford eds., Elsevier 1989, 693; S. Baba, in Chitin and Chitosan, G. Skjak-Braek, T. Anthonsen and P. Sandford eds., Elsevier 1989, 703; M. L. Marey et al., in Chitin and Chitosan, G. Skjak-Braek, T. Anthonsen and P. Sandford eds., Elsevier 1989, 713; J. Dutkiewicz et al., in Chitin and Chitosan, G. Skjak-Braek, T. Anthonsen and P. Sandford eds., Elsevier 1989, 719; K. Inouye et al., Drug Des. Deliv., 1989, 4, 55; F. Acaturk, Pharmazie, 1989, 44, 547; S. Miyazaki et al., Acta Pharm. Nord, 1990, 2, 401; R. Muzzarelli, Antimicrob. Agents Chemoter., 1990, 34, 2019; Y.D. Sanzgiri et al., Pharm. Res., 1990, 7, 18).

The literature (Kato et al., Japan Kokai Tokyo Koho 79.74885, 1979; Y. Shigeno et al., J. Appl. Pol. Sci., 1980, 25, 731; Y. Shigeno et al., Angew. Makro, Chem., 1980, 90, 1980; A. De Rosa, Italian Pat. Appln., 20482A/90) describes iodine and chitosan complexes based on a transfer of charge between the aminic group in the chitosan and the iodine molecule. These stable complexes, which can contain up to 50% of bound iodine, are obtained by suspending the polymeric material in elementary iodine solutions prepared using different types of organic solvents. Aloalcans, aliphatic and aromatic alcohols, aliphatic or aromatic ethers and ketones have been used as organic solvents in which to dissolve the iodine.

Although in theory this type of iodine and chitosan complex is potentially applicable as an iodine slow-release system for topical applications, no such use has been made up to now due to the problems encountered in industrial scale-up for preparation of these complexes, when they are obtained by suspending the polymeric material in organic solutions containing iodine. The problems encountered are connected to: a) the use of large amounts of organic solvents, which are often extremely toxic, and which are hard to re-cycle because of the presence of large amounts of residual iodine in the solution; b) the extremely long reaction times, which can be in the order of several dozen days; c) the extreme difficulty encountered in removing the solvent from the chitosan-iodine complex, so as to bring the specifications of the finished product to levels compatible with pharmaceutical use.

It has now been unexpectedly found, that it is possible to prepare charge transfer complexes of iodine and the aminic function of biopolymers, such as chitin, chitosan and derivatives thereof, in the total absence of solvents. Subject of the present invention is therefore a process for the preparation of complexes of iodine with chitosan or derivatives thereof, obtained without using solvents. A first embodiment of the process for preparation according to the invention provides for exposure of the powdered polymer to iodine vapours caused by the sublimation of elementary iodine at room temperature or above.

Formation of the complex is much quicker than the solution method, requiring only a few hours, and the material obtained can be used directly as an active principle in pharmaceutical forms without any additional purification or treatment.

By merely adjusting the relative amounts of iodine and biopolymer it is possible to obtain iodine-chitosan complexes of a pre-established stoichiometry, with iodine concentrations of up to 60–70% w/w.

As the amount of iodine increases, the chitosan tends to darken, until taking on a metal brown colour when concentrations are maximum.

The complexes obtained are extremely stable in a dry state, decomposing only at temperatures of above 200° C.

The process for preparation of the chitosansiodine complexes, using iodine in its vapour phase, can be carried out in an optimum and rapid manner in reactors of suitable geometry. The reactor, which must be made of a material capable of resisting the chemical attack of iodine in its elementary state, preferably glass, is generally characterized by the fact that it comprises two compartments, the first one being maintained at a high temperature (70°–100° C.) and in which the iodine vapour is generated, whereas in the second one, kept at room temperature, contact between the iodine in its vapour phase and the powdered biopolymer takes place.

An example of a reactor used for preparation of the iodine-chitosans complexes according to the process of the invention has the following characteristics. The apparatus is made up of two wide-necked pyrex glass bottles (diameter of the threaded mouth 6 cm), connected together by a teflon or graphite connector. The smaller container, which holds the iodine, has a diameter of 8 cm and a height of 25 cm, whereas the larger container, which holds the chitosan, has a diameter of 30 cm and a height of 45 cm. To prepare the complex, elementary iodine is introduced into the smaller compartment and chitosan of a suitable granulometry (preferably between 20 and 200 μm in diameter) is introduced into the larger one. After having connected the two containers using the teflon connector, the reactor is rotated slowly around its axis, using a roller rotator giving a rotation speed not exceeding 50 r/p/m., preferably between 10 and 30 r/p/m. The smaller compartment is heated by a quartz resistor placed parallel to the reactor. Control of the temperature, which is generally maintained between 70° and 100° C, takes place by modifying the distance between the resistor and the iodine container and the power supply. This guarantees rapid sublimation of the iodine, the yapours of which, passing into the the larger container at room temperature, combine in an effective manner with the chitosan, creating in just a few hours a compound with homogeneous characteristics, with a stoichiometry dependent on the ratio by weight of iodine to chitosan.

The general characteristics of the process according to the invention and the simple construction of the reactor described above render the preparation of iodine/chitosans complexes in a dry state with the iodine in its vapour phase extremely economical, capable of easy industrial scale-up even to levels of hundreds of Kg of treated material. In effect, the process can easily be used even by non-qualified personnel, in environments of a modest size, in which the complex and expensive requirements prescribed by industrial safety and environmental pollution regulations are not necessary.

An even more simple embodiment of. the process according to the present invention for the preparation of chitosans/ iodine complexes provides for mixing together, at suitable ratios, amounts of chitosan or derivatives thereof with iodine in its elementary state at room temperature. The iodine, sublimating slowly, fixes itself to the chitosan, causing formation of the complex. Obviously, reaction times are much longer than those found using the heated reactor, as much as 3–5 days being required to complete the reaction, which can be seen by the brown colour taken on by the chitosan and by the fact that the iodine crystals disappear.

An even sipler method for the preparation of iodine-chitosan complexes is based on the quick mixing in an homogenizer of chitosan and iodine, which is reduced in microcrystals and therefore sublimates quickly forming the complex.

The chitosan-iodine complexes thus formed, if the percentage content of iodine does not exceed 50% (w/w), can be dissolved in aqueous solvents of an acid nature, for example diluted acetic acid or glutamic acid, producing viscous solutions of a brown colour that do not stain the skin, in which the iodine remains stable in the form of a soluble complex with chitosan. Solubilization takes place at room temperature and requires on average 24–48 hours. The use of the preformed complex in its solid state appears to be of critical importance in order to obtain the chitosan-iodine complex in solution. In fact, the addition of elementary iodine to a solution of chitosan in an acid solvent does not cause formation of the soluble complex, even after weeks. Said solutions are compatible with the addition of surfactants, preferably of a non-ionic type, such as Tween or Brij, which improve the solubility of the chitosan-iodine complex, changing its colour to a yellow-orange.

In the presence of surfactants, even in concentrations of below 1% w/v, it is possible to solubilize chitosan-iodine complexes that are normally insoluble in acid solutions, as they have a composition of over 50% (w/w) iodine.

Solutions with characteristics identical to those described above can be prepared by solubilizing the iodine in a suitable surfactant, preferably non-ionic, heated if necessary, and adding this solution, under rapid stirring, to the chitosan or derivatives thereof or their salts dissolved in water, optionally in the presence of acids or salts.

Alternatively, formation of the chitosan-iodine complex, assisted by the presence of the surfactant, can be done by adding the chitosan or derivatives thereof or their salts as a dry powder to the concentrated solution of iodine in the surfactant. In just a few minutes the iodine adsorbs onto the chitosan, producing an oily powder of a dark brown colour made up of the chitosan-iodine complex and the surfactant. This material, when suspended in water or acid solutions, preferably acetic acid or glutamic acid, solubilizes in a few minutes to give the chitosan-iodine complex of an orange-yellow colour. The viscosity of these solutions depends on the molecular weight and the amount of chitosan used.

The complexes of iodine with chitosans, prepared according to the process of the invention, both in their dry state and in solution, act as halogen slow release systems, showing a notable bactericidal and micticidal action against numerous types of microorganism that commonly infect the skin and wounds, such as, for example, *Staphylococcus aureus, Saphylococcus epidermis, Staphylococcus haemolyticus, Salmonella enteridis, Klebsiella pneumoniae, Proteus mirabilis, Pseudomonas aeruginosa, Streptococcus pyogenes, Escherichia coli, Serratia marcescens, Candida tropicalis,* Enterobacter and Citrobacter.

The absence of inflammatory phenomena, the disinfectant action and the beneficial action on the process of cicatrization of wounds, connected with use of the complexes according to the invention, are clearly evident on rats subjected to xipho-pubic laparatomy. In the animals operated the surgical wound is subsequently sutured on the muscular and skin structures and the wound of part of the rats is medicated by aspersion of the chitosan-iodine complex in powder form, which shows excellent adhesion to the tissues and high coverage. When compared to the controls, the treated animals show an absence of infective processes and a quicker cicatrization process, which is evident as early as the second day.

The release of iodine from the polymeric matrix, when the complex is applied to the wound and rendered humid by the exudations, tan easily be seen from the gradual discolouration of the powder. In fact the iodine, once released, is gradually transformed into colourless chemicals as it performs its disinfectant activity.

For this reason the complexes of iodine with chitosan and derivatives thereof, in the form of powders, solutions and ointments, due to their disinfectant and cicatrizing properties can be used in the medical and surgical field in postoperative treatment and more generally as products for topical use in the medication of wounds and the disinfection of the skin. In particular the soluble forms, when applied to the skin, due to the exceptional filmogenous powers of complexes of iodine with chitosan or derivatives thereof, give rise to a film of iodinated biopolymer which, in a uniform and prolonged manner, guarantees an effective disinfectant action without leaving stains or damaging the skin. The polymeric film can later be removed with ease by washing the treated part with water.

Subject of the present invention are therefore also pharmaceutical compositions containing as active principle at least one of the polymeric iodine-based compounds of the general formula indicated above, optionally mixed with excipients conventionally used in pharmaceutical practice. In particular, the complexes according to the present invention can be used, in the form of powders, solutions, plasters and ointments, for the medication of open sores or bedsores and wounds, in particular those connected with surgical operations, in which the combination of the cicatrizing action and the extended disinfectant action are of particular advantage.

Another field of interest in which the complexes according to the invention can be used as active principles is the parasanitary and cosmetic field, for example in the preparation of new talcum powders, deodorant powders, cleansing and disinfectant solutions, and so on.

The examples given in the following illustrate the processes of preparation of different types of chitosan containing iodine both in a dry state and in solution, and they give evidence of its disinfectant and cicatrizing action. Of necessity, they only contemplate some of the numerous possibilities that may be envisaged and, without any intention to limit the scope thereof, they are intended to define the area to which the present invention relates.

EXAMPLE 1

A cylindrical reactor is used, made up of two wide-necked pyrex glass bottles (diameter of threaded neck 6 cm) fastened together using a teflon connector. The smaller container, in which the iodine is placed (200 g), has a diameter of 8 cm and a height of 25 cm, whereas the larger container, in which the chitosan is placed (1.8 Kg, with an average molecular weight of 8 KD, in which the number of acetilated residues of 2-amino-2-deoxy-β-D-glycan acetilates does not exceed 5% of the total number of monomeric units present, and with a granulation of 20–200 μm), has a diameter of 30 cm and a height of 45 cm. After having joined the two containers together by means of the teflon connector, the reactor is put into slow rotation along its axis, using a roller rotator which imparts a rotation speed of 10 r/p/m. The smaller compartment is heated to approximately 100° C. by a quartz resistance placed parallel to the reactor. The temperature is controlled by modifying the distance of the resistance from the container holding the iodine and the supply power. This guarantees rapid sublimation of the iodine, the vapours of which, passing into the larger container at room temperature, combines effectively with the chitosan, giving in 5 hours the formation of 2 Kg of chitosan-iodine complex in the form of an homogeneous powder of a slightly brownish colour, with an iodine content of 10% (w/w). The complex, when subjected to thermal analysis, shows a decomposition point of around 205° C. The FT-IR in KBr shows the presence of signals characteristic of the functional groups of chitosan (NH, OH, CO). Elementary analysis indicates the following percentages C 44.44%, H 6.13% O 35.80%, N 7.74% and I 9.89%, which agree with the degree of acetilation of the chitosan employed (5%) and with the percentage of iodine present (10%). X-ray diffractometric analysis of the powder indicates that the complex prepared has an amorphous structure in which there are.no evident diffraction planes. The material, kept at 25° C. in a high vacuum for 48 h or under atmospheric pressure in an open container for 4 months, shows no weight loss, confirming the great stability of the chitosan/iodine complex thus prepared.

EXAMPLE 2

The procedure is the same as that given in Example 1, but the iodine and the chitosan are stirred together at room temperature in a pirex container with a diameter of 30 cm and a height of 45 cm. The bottle is kept under rapid rotation (50 r/p/m) as indicated in Example 1. The formation of the complex is completed in approximately 3 days, as indicated by the brownish colour taken on by the chitosan and the disappearance of the iodine crystals. The chemical and physical characteristics of the chitosan-iodine complex thus obtained are the same as those given in Example 1.

EXAMPLE 3

2 Kg of chitosan (20–200 µm; average molecular weight 8 KD; 5% acetilation of the amine groups of 2-amino-2-deoxy-β-D-glycan) and 2 Kg of elementary iodine in flakes are homogenized in a mixer for 10 minutes. 4 Kg are obtained of a brown powder which is kept in an air-tight container for 5 days, in order to complete the formation of the complex which has the same characteristics as indicated in Example 1 as regards the thermal stability of the complex, the infra-red spectroscopy and the X-ray diffraction, while elementary analysis, in accordance with the degree of acetilation and the amount of iodine present, shows the following percentage composition: C 22.40%; H 3.42%; O 19.89%; N 4.29%; I 49.98%.

EXAMPLE 4

The procedure is the same as that indicated in Example 1, using 1.8 Kg of N-carboxylbutyl chitosan in powder form (80–250 µm), with an average molecular weight of 10 KD, in which 80% of the monomeric units are represented by 2-N-carboxybutyl-2-deoxy-β-D-glycan, 15% by 2-acetamido-2-deoxy-β-D-glycan and 5% by 2-amino-2-deoxy-β-D-glycan. 2 Kg of product are obtained, having the same characteristics as indicated in Example 1 as regards the thermal stability of the complex, the infra-red spectroscopy and the X-ray diffraction, while elementary analysis, in accordance with the polymer structure and the amount of iodine present, shows the following percentage composition: C 43.36%; H 6.18%; O 35.12%; N 5.44%; I 9.87%.

EXAMPLE 5

200 g of the chitosan/iodine complex, prepared according to the process illustrated in Example 1, are dissolved in 1.8 l of an aqueous solution of 1% acetic acid (w/w). Solubilization, which is assisted by continuous stirring of the suspension, is completed in approximately 48 h at room temperature. 2 Kg of a slightly viscous solution are obtained, with a pH of 4.8 and a slightly brown colour, whose elementary iodine content, determined by titration using thiosulphate, is 0.1% (w/w). Keeping the solution in dark containers at room temperature no significant variation in iodine titer or in viscosity can be seen over a period of time.

EXAMPLE 6

According to the process illustrated in Example 5, 600 g of chitosan/iodine complex and 1.4 Kg of acetic acid solution are used. After 60 h under stirring at room temperature 2 Kg of a very viscous solution with a pH of 4.9 are obtained, brown in colour, with an elementary iodine content, determined by titration using thiosulphate, is 0.3% (w/w). Keeping the solution in dark containers at room temperature no significant variation in iodine titer or in viscosity can be seen over a period of time.

EXAMPLE 7

The process according to Example 5 is used, but 40 g of Tween 20 (polyoxyethylensorbitanmonolaurate) are added to the solution. In the presence of the surfactant the process for dissolution of the chitosan/iodine complex is completed in approximately 30 minutes and the solution takes on a yellow-orange colour.

EXAMPLE 8

100 g of iodine are solubilized at 80° C. in 500 g of Tween 20. In a few minutes an intense brown solution is obtained, to which are added 100 g of chitosan glutamate (average molecular weight 8 KD; degree of residual acetilation less than 5%; granulation 20–200 µm). In less than 5 minutes the iodine is adsorbed onto the chitosan powder, forming the chitosan/iodine complex of a brown colour, which is oily to the touch because of the presence of the adsorbed surfactant. To this material are added 9,3 Kg of water. Rapid solubilization of the complex is observed, which is completed in less than 1 hour, with formation of a viscous solution of a yellow-orange colour. The titer in elementary iodine, determined by titration using thiosulphate, is 1% by weight. On keeping the solution in dark containers at room temperature no significant variation in iodine titer or in viscosity are noted.

EXAMPLE 9

50 g. of chitosan/iodine complex containing 60% (w/v) of elementary iodine, prepared by adsorbing 30 g of iodine onto 20 g of chitosan (average molecular weight 8 KD; degree of residual acetilation less than 5%, granulation 20–200 µm) according to the method given in Example 1, are suspended in 930 g of an aqueous solution of 1% acetic solution (% by weight). 20 g of Tween 20 are added to the suspension under rapid stirring. In less than one hour the complete solubilization of the chitosan/iodine complex can be observed, with the formation of a solution of an intense orange colour, slightly viscous. The elementary iodine titer, determined by titration using thiosulphate, is 3% (w/w). On keeping the solution in dark containers at room temperature no significant variation in iodine titer or in viscosity are noted.

EXAMPLE 10

40 g. of iodine are solubilized at 80° C. in 200 g of Brij 56. In a few minutes an intense brown solution is obtained which, under energetic stirring, is additioned to 9.76 Kg of an aqueous solution of 3% by weight chitosan (molecular weight 8 KD; degree of residual acetilation less than 5%; granulation 20–200 μm) in 1% acetic acid (w/w). The formation of the yellow-orange chitosan/iodine complex is immediately observed. The titer in elementary iodine, determined by titration using thiosulphate, is 0.4% (w/w). On keeping the solution in dark bottles at room temperature no significant variation in iodine titer or in viscosity are noted.

EXAMPLE 11

It is known that iodine complexes act as antibacteric agents because of the presence of free or readily available iodine. In the case of the chitosan/iodine complexes according to the invention, an overall equilibrium of the following type exists: CHITOSAN-IODINE COMPLEX⇌CHITOSAN+IODINE which is responsable for the activity of the complex.

Given the low solubility of chitosan/iodine complexes in non-acid aqueous media, it was decided to compare the iodine release rate from these complexes with that from iodine-polyvinylpyrrolidone complexes which, as is known, form the active base of antiseptic compounds in use for many years (Betadine, Breunol, Inadine, etc.).

The iodine release rate was evaluated by dosing the iodine using sodium thiosulphate titration, using starch as an indicator, as described in USP XXI, pag. 863.

Amounts giving an equivalent iodine content (approx. 0.05 M) of the iodine/polyvinylpyrrolidone complex and the chitosan/iodine complex were used. Titration was performed under magnetic stirring at 25° and 37° C.; the progress of the titration curves over a period of time shows that:
a) the iodine/polyvinylpyrrolidone complex renders the total amount of iodine available within a period of 40 minutes at 25° C. and of 30 minutes at 37° C.;
b) the chitosan/iodine complex, under the same conditions, releases 50% of the available iodine over 2 h at 25° C. and over 90 min. at 37° C.;
c) extending the period of time it is observed that the release of iodine from the chitosan/iodine complexes at 25° C. has not been completed even after 24 h whereas at 37° C. the iodine is completely released over the same period.

The tests carried out have shown clearly that the release of iodine from the chitosan/iodine complex in its suspended solid phase is much more gradual that that characterizing the iodine/polyvinylpyrrolidone complex in solution, in fact in the former case the overall equilibrium that is formed is the following:

```
A) CHITOSAN–IODINE COMPLEX ← → CHITOSAN/IODINE COMPLEX
         (solid)                      (solution)
B) CHITOSAN/IODINE COMPLEX ← → CHITOSAN + IODINE
         (solution)
``` in which the slow stage is represented by the reaction A. These data taken as a whole demonstrate that the chitosan/ iodine complexes in powder form, because of the gradual release of the active iodine characterizing them, act as highly effective long-lasting and controlled anti-bacterial agents.

EXAMPLE 12

Amounts of the chitosan/iodine complexes corresponding to 0.2, 0.3 and 0.4 mg of bound iodine, prepared as indicated in Examples 1 and 3, are placed on disks of filter paper with a diameter of 0.5 cm. The above disks are deposited on the surface of agar plates containing standard culture media for growth of the following microorganisms: *Staphylococcus aureus, Staphylococcus epidermis, Staphylococcus haemolyticus, Salmonella enteridis, Klebsiella pneumoiae, Proteus mirabilis, Pseudomonas aeruginosa, Streptococcus pyogenes, Escherichia coli, Serratia marcescens* and *Candida tropicalis*. Filter paper disks loaded with equivalent amounts of polymer containing no iodine are used as controls. After having inoculated the plates with the various microorganisms, they are incubated for 12 h. The antibacterial activity of the polymers containing iodine is evaluated from the inhibition rings measured around the paper disks. No significant differences are noted between the two types of chitosan/iodine complex, whereas the chitosan alone shows no significant inhibition of growth in the various microorganisms under examination. The inhibitory effect increases proportionally to the dose, showing an approximately two-fold increase in diameter from the lowest dose to the highest one. The best inhibitory effect is obtained with *Staphylococcus aureus, Staphylococcus epidermis* and *Proteus mirabilis*, with an inhibition ring of over 10 mm at maximum dosage.

EXAMPLE 13

The activity of the chitosan/iodine complex, prepared as described in Example 1, in powder form and in solution, was evaluated by comparison with a commercial preparation based on a water-soluble iodine/polyvinylpyrrolidone complex, with the same concentrations of iodine.

The experiment aimed at determining the bacteriocidal and micetocidal times, was carried out on 30 strains of Gram-positive and Gram/negative bacterial species of recent clinical isolation, and on 5 strains of mycetes.

A solution in distilled water containing 0.75% of iodine was prepared of the iodine/polyvinylpyrrolidone complex, and a solution of similar concentration in of the chitosan/ iodine complex prepared as described in Example 8 was prepared, while a suspension of the chitosan/iodine complex in powder form prepared as described in Example 1 was prepared in distilled water containing the same concentration.

These preparations were distributed as prepared, or diluted 1:10 v/v in bi-distilled water, in amounts of 0.9 ml, in sierology test tubes, to which 0.1 ml of the various bacterial suspensions were added, diluted 1:100 v/v in physiological solution, cultivated for 12 h at 37° C. in Brain Heart Infusion Broth in the case of the bacteria, and for 48 h at 26° C. in Sabouraud Broth in the case of the mycetes.

After 1, 5, 10 and 20 minutes of contact between the germs and the iodinated compound under examination, using a calibrated loop, 0.01 ml was taken from the various test tubes and poured into 10 ml of Letheen Broth. After incubation for 24 h at 37° C. for the bacteria and 48 h at 26° C. for the mycetes, growth of the various germs was evaluated and the interval of time corresponding to absence of growth was considered to be the inactivation time. As the data in Table 2 show the chitosan/iodine complex, even in insoluble form, has a strong cytocide activity, comparable with that of the water soluble iodine/polyvinylpyrrolidone complex.

This demonstrates that in the presence of water the iodine present in the chitosan/iodine complex is released and performs its disinfectant activity effectively.

Mueller Hinton Broth containing 0.5% carboxymethylcellulose was used as a culture medium, in order to aid in maintaining the chitosan/iodine complex in suspension when used as a powder.

Base solutions of the chitosan/iodine complex, both in powder and in solution, were prepared by additioning the complex directly to the culture broth at a concentration of 0.15% (w/w) iodine. From this solution were subsequently prepared solutions with a lower iodine content, diluting the base solution 5, 10, 20, 40, 80 and 160 times with culture medium. A similar process was used to prepare solutions of the iodine/polyvinylpyrrolidone complex at different concentrations of iodine.

Amounts of 2 ml of the various solutions were inoculated with 0.1 ml of bacterial suspension obtained by diluting

TABLE 2

Cytocide times for iodine/polyvinylpyrrolidone and iodine/chitosan complexes

| Microorganisms | Strains N° | Dilution | 1' PVI | 1' CHS | 1' CHP | 5' PVI | 5' CHS | 5' CHP | 10' PVI | 10' CHS | 10' CHP |
|---|---|---|---|---|---|---|---|---|---|---|---|
| | | | No. germs inactivated at the various times | | | | | | | | |
| Stafilococcus aureus | 6 | as such | 6 | 6 | 6 | | | | | | |
| | | 1:10 | 5 | 6 | 6 | 6 | | | | | |
| Stafilococcus epidermis | 4 | as such | 4 | 4 | 4 | | | | | | |
| | | 1:10 | 4 | 4 | 4 | | | | | | |
| Salmonella spp | 4 | as such | 2 | 3 | 3 | 4 | 4 | 4 | | | |
| | | 1:10 | 1 | 3 | 2 | 2 | 4 | 3 | 4 | | 4 |
| Pseudomonas aeruginosa | 3 | as such | 1 | 2 | 2 | 3 | 3 | 3 | | | |
| | | 1:10 | 0 | 1 | 0 | 2 | 3 | 2 | 3 | | 3 |
| Proteus spp | 4 | as such | 2 | 2 | 1 | 4 | 4 | 4 | | | |
| | | 1:10 | 1 | 3 | 2 | 2 | 4 | 3 | 4 | | 4 |
| Escherichia coli | 5 | as such | 5 | 5 | 5 | | | | | | |
| | | 1:10 | 1 | 3 | 2 | 5 | 5 | 5 | | | |
| Klebsiella spp | 2 | as such | 1 | 2 | 1 | 2 | | 2 | | | |
| | | 1:10 | 0 | 1 | 0 | 1 | 2 | 1 | 2 | | 2 |
| Serratia marcescens | 2 | as such | 1 | 1 | 1 | 2 | 2 | 2 | | | |
| | | 1:10 | 0 | 0 | 0 | 0 | 1 | 0 | 2 | 2 | 2 |
| Candida albicans | 5 | as such | 1 | 2 | 1 | 5 | 5 | 5 | | | |
| | | 1:10 | 1 | 1 | 1 | 2 | 4 | 3 | 5 | 5 | 5 |

PVI = water soluble iodine/polyvinylpyrrolidone complex; CH = chitosan/iodine complex

EXAMPLE 14

Activity Of the chitesan/iodine complex in powder form, prepared as described in Example 1, and in solution, prepared as described in Example 8, is evaluated by comparison with a commercial preparation based on a water soluble iodine/polyvinylpyrrolidone complex, at equal iodine concentrations.

The experiment, aimed at determining the minimum inhibiting concentration (M.I.C.), was performed on 65 strains of Gram-positive and Gram-negative bacterial species of recent isolation.

cultures of the various strains of bacteria grown for 12 h at 37° C. 1:100 (v/v) in physiological solution.

The results were read after 24 h of incubation at 37° C.

As can be seen from the data shown in Table 3, the chitosan/iodine complex, both as a powder and as a solution, has high anti-bacterial activity. In fact, the Gram-positive bacteria were all inhibited up to a dilution of 1:40, whereas the Gram-negative bacteria were all inhibited at a dilution of 1:5, This type of result appears comparable with that observed for the soluble iodine/porvinylpyrrolidone complex,

TABLE 3

M.I.C. for various strains of bacteria of chitosan/iodine and iodine/polyvinylpyrrolidone complexes

| Strain | str. N° | compound (*) | N° strains inactivated at the dilution level | | | | | | |
|---|---|---|---|---|---|---|---|---|---|
| | | | 1:5 | 1:10 | 1:20 | 1:40 | 1:80 | 1:160 | 1:320 |
| Stafilococcus aureus | 20 | PVI | 20 | 20 | 20 | 20 | 2 | 0 | |
| | | CHS | 18 | 16 | 14 | 14 | 1 | 0 | |
| | | CHP | 20 | 20 | 20 | 20 | 3 | 0 | |

TABLE 3-continued

M.I.C. for various strains of bacteria of
chitosan/iodine and iodine/polyvinylpyrrolidone complexes

| Strain | str. N° | compound (*) | N° strains inactivated at the dilution level ||||||| 
| | | | 1:5 | 1:10 | 1:20 | 1:40 | 1:80 | 1:160 | 1:320 |
|---|---|---|---|---|---|---|---|---|---|
| *Stafilococcus epidermis* | 5 | PVI | 5 | 5 | 5 | 5 | 5 | 1 | 0 |
| | | CHS | 4 | 4 | 3 | 3 | 2 | 0 | |
| | | CHP | 5 | 5 | 5 | 5 | 5 | 2 | 0 |
| Salmonella spp | 7 | PVI | 7 | 7 | 4 | 2 | 0 | | |
| | | CHS | 6 | 5 | 3 | 2 | 0 | | |
| | | CHP | 7 | 7 | 5 | 1 | 0 | | |
| *Pseudomonas aeruginosa* | 5 | PVI | 5 | 3 | 1 | 0 | | | |
| | | CHS | 4 | 2 | 0 | 0 | | | |
| | | CHP | 5 | 3 | 2 | 0 | | | |
| Proteus spp | 8 | PVI | 8 | 6 | 3 | 1 | 0 | | |
| | | CHS | 7 | 5 | 2 | 0 | | | |
| | | CHP | 8 | 8 | 6 | 0 | | | |
| *Escherichia coli* | 8 | PVI | 8 | 5 | 4 | 0 | | | |
| | | CHS | 7 | 4 | 2 | 0 | | | |
| | | CHP | 8 | 5 | 3 | 0 | | | |
| Klebsiella spp | 4 | PVI | 4 | 3 | 1 | 0 | | | |
| | | CHS | 3 | 1 | 0 | | | | |
| | | CHP | 4 | 2 | 1 | 0 | | | |
| Enterobacter spp | 4 | PVI | 4 | 3 | 1 | 0 | | | |
| | | CHS | 3 | 1 | 0 | | | | |
| | | CHP | 4 | 3 | 1 | 0 | | | |
| Serratia spp | 2 | PVI | 2 | 2 | 0 | | | | |
| | | CHS | 2 | 2 | 0 | | | | |
| | | CHP | 2 | 2 | 1 | 0 | | | |
| Citrobacter spp | 2 | PVI | 2 | 2 | 1 | 0 | | | |
| | | CHS | 1 | 1 | 0 | | | | |
| | | CHP | 2 | 2 | 1 | 0 | | | |

PVI = iodine/polyvinylpyrrolidone complex; CHP = chitosan/iodine complex powder in suspension;
CHS = chitosan/iodine complex solution

EXAMPLE 15

30 rats of both sexes, with an average weight of approximately 250 g, after anesthaesia with ketalar and atropina, were shaved and subjected to a xifo-pubic laparatomy of approximately 10 cm in length.

Subsequently the muscular and the cutaneous layers of the surgical wound were sutured, with medication, both at the level of the muscle suture and at that of the skin suture, of 10 animals by sprinkling on the wound 50 mg of the chitosan/iodine complex prepared as described in Example 1, and 10 animals by sprinkling on the wound 50 mg of chitosan alone, not charged with iodine.

During the following days the skin suture only was medicated in these 20 animals, using the same amounts of chitosan/iodine complex. On days 2, 5 and 13 samples of tissue for histological analysis were taken from the 10+10 animals treated, respectively, with the chitosan/iodine complex and with chitosan alone, and from a further 10 unmedicated controls.

In the animals treated with the chitosan/iodine complex it was observed, both following macroscopic examination and on the basis of the histological samples, that there was an absence of infective processes in the wound, which were on the contrary frequently found in the animals treated with chitosan alone or left untreated. Furthermore, as early as day 2, the cicatrization process appears more effective in the animals medicated with the chitosan/iodine complex when compared with the unmedicated controls, and this difference becomes much more evident on days 5 and 13.

As a whole, treatment with the chitosan/iodine complex shows itself to guarantee effective asepsis of the wound and to accelerate the healing process, with a cicatrization process showing a larger preponderance of cell healing elements and a more rapid elimination of necrotic waste.

EXAMPLE 16

The chitosan/iodine complexes can be used as active principles in pharmaceutical products with antiseptic and wide-ranging antibacterial action, to be used electively in the disinfection of wounds, abrasions, burns and in surgical medication.

The following Table 4 shows examples of pharmaceutical compositions containing the chitosan/iodine complex as active principle, and chitosan, zinc oxide and talc as optional additional components.

TABLE 4

Examples of pharmaceutical compositions
containing the chitosan/iodine complex as active principle.

| | Chemical components (% w/w) ||||
| | chitosan/iodine* | chitosan° | zinc oxide^ | talc^ |
|---|---|---|---|---|
| Preparation 1 | 10 | 90 | | |
| Preparation 2 | 10 | 5 | 5 | 80 |
| Preparation 3 | 9 | 10 | 5 | 76 |

*Chitosan/iodine complex 10% w/w, prepared as described in Example 1
°Chitosan with the same specifications indicated in Example 1
^Pharmaceutical product

EXAMPLE 17

The pharmacodynamic evaluation of the preparations described in Example 16, in terms of spectrum and rate of action, was tested over a series of microorganisms selected from among the most common in the nosocomial range, such as: *Stafilococcus epidermis, Enterobacter cloacae, Serratia marcescens, Pseudomonas aeruginosa, Proteus mirabilis, Escherichia coli, Stafilococcus aureus* and *Candida albicans.*

The disinfactant power of the preparations, both in solution and on solid medium, was evaluated over a period of time using the following culture media:

Nutrient Agar, used for cultivation of the bacteria

Sabouraud Agar, used for cultivation of *Candida albicans*

Tryptic Soy Agar with the addition of sodium thiosulphate 1% w/w and Tween 80 1% w/w to neutralize the disinfectant action of the iodine Tryptic Soy Broth, with the addition of neutralizing agent as for Tryptic Soy Agar Sabouraud Agar with the addition of neutralizing agent as for Tryptic Soy Agar Sabouraud Liquid Medium with the addition of neutralizing agent agent as for Tryptic Soy Agar.

Before running the experiment, a test was carried out to see whether or not the neutralizing agent was actually capable of blocking the activity of the disinfectants under examination.

With this object, Petri plates were prepared for each disinfectant, in which 10 mg of disinfectant was incorporated in 20 ml of test medium. On these plates and on similar plates of Tryptic Soy Agar with no disinfectant and neutralizing agent, used as controls, the various strains of bacteria were implanted using a spatula, so that each plate Contained approximately 300 colonies.

After incubation at 37° C. for 48 h, it was observed that there was no significant difference in the number of bacterial colonies formed on the control plates and on those with disinfectant and neutralizing agent.

The microorganisms subjected to the experiment were obtained by 24 h subculture on Nutrient Agar for bacteria, and on Sabouraud Agar for Candida albicans. The microorganisms were collected in sterile physiological solution, washed and centrifugated spun twice, and finally re-suspended until obtaining a torbidity equal to a barium sulphate standard corresponding to a concentration of approximately $10^6$ ufc/ml.

Torbidity was measured using spectrophotometry, at optical density, at a wavelength of 640 nm.

At the moment of testing an overall count was performed on each microbic suspension, using the method of successive dilution and incorporation in Triptic Soy Agar.

Determination of anti-bacterial activity was carried out as described below. For each microorganism 2 ml of suspension were placed in contact with 160 mg of formulation. After 30", 1'and 2'of contact 0.1 ml was taken from each suspension-and distributed in 10 ml of Tryptic Soy Broth+ neutralizing agent. The tests were carried out in duplicate.

The results, which are given in Table 5, were obtained after incubation for 48 h at 37° C.

TABLE 5

Data an the antimicrobic activity of formulations containing chitosan/iodine complexes as active principle

| sample tested | preparation 1 | | | | preparation 2 | | | | preparation 3 | | | |
|---|---|---|---|---|---|---|---|---|---|---|---|---|
| contact time | 30" | 1' | 2' | 5' | 30" | 1' | 2' | 5' | 30" | 1' | 2' | 5' |
| *Stafilococcus aureus* | ++ | ± | – | – | + | ± | – | – | ++ | ± | ± | – |
| *Enterobacter cloacae* | + | – | – | – | + | – | – | – | + | – | – | – |
| *Escherichia coli* | + | ± | – | – | + | – | – | – | + | ± | – | – |
| *Serratia marcescens* | + | – | – | – | + | – | – | – | + | ± | – | – |
| *Pseudomonas aeruginosa* | + | – | – | – | + | ± | – | – | + | ± | – | – |
| *Proteus mirabilis* | + | – | – | – | + | – | – | – | + | ± | – | – |
| *Candida albicans* | + | ± | – | – | + | ± | – | – | ++ | ± | ± | – |

The composition of Preparations 1, 2 and 3 are given in Example 12. The symbol (–) means lack of growth; the symbol (+) means presence of growth; the symbol ( ) means very moderate growth.

EXAMPLE 18

Trans-cutaneous toxicity of the preparations 1, 2 and 3, described in Example 16, and of the solutions described in Examples 6–8 on whole, scarified skin was tested on male Canada white rabbits. For each sample the experiment was carried out on 4 animals with whole skins and 4 animals with scarified skins. The product was applied by rubbing the skin in the case of powders and by brushing in the case of solutions.

Blood samples were taken from the animals before application commenced, in order to perform the following chemical and clinical tests, which were then repeated 2 days after application of the samples: triglycerides; alkaline phosphatase; bilirubin; creatinin; uric acid; ureic nitrogen; glucose determined enzymatically; cholesterol determined enzimatically; inorganic phosphur; calcium; total proteins; iron.

Macroscopic and hystologic observation of the animals under treatment showed the absence of particular abnormalities and irritative processes. Furthermore, comparison of the analytical data before and after treatment with the sample on animals with whole and scarified skins showed absence of any significant variation. These data as a whole demonstrate that the formulations based on chitosan-iodine complexes in powder form and in solution have no harmful or toxic effects, show excellent tolerability, do not show systemic action and therefore have an exclusively local effect.

We claim:

1. A process for the preparation of a charge transfer complex of iodine with chitosan or a derivative thereof wherein the chitosan or the derivative thereof and the iodine are made to react in the absence of solvent.

2. A process for the preparation of a charge transfer complex of iodine with chitosan or a derivative thereof according to claim 1, in which the chitosan or derivative thereof is in powder form and is treated with the iodine in vapor phase.

3. A process for the preparation of a charge transfer complex of iodine with chitosan or a derivative thereof according to claim 1, in which the chitosan or derivative thereof is mixed with the iodine in its elementary state at room temperature.

4. A process for the preparation of charge transfer complexes of iodine with chitosan or a derivative thereof, wherein the iodine is dissolved in a surfactant, and the resulting solution is either added to an aqueous solution of chitosan, or adsorbed onto water-soluble chitosan in powder form.

5. A charge transfer complex of iodine with chitosan or a derivative thereof, obtainable using the process according to claim 1, containing iodine in a proportion that is expressed by the general formula:

$$X(I_2)_n$$

in which

X is a monomeric unit of a polymer selected from the group consisting of chitin, chitosan, N-carboxybutyl-chitosan, N-acylchitosans, N-carboxymethylchitosan, N-O-carboxymethylchitosan, N-O-chitosan sulfate, and their salts, and n is a number variable from 0.01 to 1.5.

6. A charge transfer complex of iodine with chitosan or a derivative thereof according to claim 5, in which X is selected from the group consisting of the following monomeric units:

2-amino-2-deoxy-β-D-glycan; 2-acetamido-2-deoxy-β-D-glycan; 2-N-carboxymethylamino-2-deoxy-β-D-glycan; 2-N-acylamino-2-deoxy-β-D-glycan; 2-N-carboxymethylamino-2-deoxy-β-D-glycan; 2-N-carboxymethylamino-2-deoxy-β-D-6-O-carboxymethylglycan; 2-N-dihydroxypropylamino-2-deoxy-β-D-glycan; 2-amino-2-deoxy-β-D-glycan N-sulfate; and 2-amino-2-deoxy-β-D-glycan O-sulfate.

7. A charge transfer complex of iodine with chitosan or a derivative thereof, according to claim 6, in which the acyl group of 2-N-acylamino-2-deoxy-β-D-glycan is selected from the group consisting of propionyl, butyryl, caproyl, oxalyl, succinyl and phthalyl.

8. A charge transfer complex of iodine with chitosan or a derivative thereof according to claim 5, in the form of an aqueous solution, containing a surfactant, and optionally acidified.

9. A pharmaceutical composition with disinfectant and cicatrizing activity, containing as active principle the charge transfer complex of iodine with chitosan or a derivative thereof according to claim 5, in solution or in a dry state, optionally mixed with conventional excipients.

10. A pharmaceutical composition according to claim 9, in the form of a powder, solution, membrane, plaster or ointment.

11. In a method of applying a medicament with disinfectant and cicatrizing activity to skin, the improvement wherein a component of said medicament is a charge transfer complex of iodine with chitosan or derivative thereof according to claim 5.

12. In a method of making a disinfectant and deodorant powder or disinfectant solution which forms a protective film when applied to the skin, for a pharmaceutical and cosmetic purpose, comprising mixing components to form said powder or solution, the improvement wherein a said component is a charge transfer complex of iodine with chitosan or derivative thereof according to claim 5.

13. A charge transfer complex of iodine with chitosan or a derivative thereof, according to claim 6, in the form of an aqueous solution, containing a surfactant, and optionally acidified.

14. A pharmaceutical composition with disinfectant and cicatrizing activity, containing as active principles the charge transfer complex of iodine with chitosan or derivative thereof according to claim 13, in solution or in a dry state, optionally mixed with conventional excipients.

15. A charge transfer complex of iodine with chitosan or a derivative thereof, according to claim 7, in the form of an aqueous solution, containing a surfactant and optionally acidified.

16. A pharmaceutical composition with disinfectant and cicatrizing activity, containing as active principle the charge transfer complex of iodine with chitosan or derivative thereof according to claim 15, in solution or in a dry state, optionally mixed with conventional excipients.

17. In a method of making a medicament with disinfecting and cicatrizing activity comprising mixing components to form said medicament, the improvement wherein a said component is a charge transfer complex of iodine with chitosan or derivative thereof according to claim 8.

18. In a disinfectant and deodorant powder or disinfectant solution which forms a protective film when applied to the skin, in a pharmaceutical or cosmetic composition form, the improvement wherein said composition includes a charge transfer complex of iodine with chitosan or a derivative thereof, in accordance with claim 6.

19. A process according to claim 4 wherein said surfactant is non-ionic.

20. A charge transfer complex according to claim 8 wherein said aqueous solution is acidified with acetic acid or glutamic acid.

21. A solution according to claim 8 wherein said surfactant is non-ionic.

22. A charge transfer complex according to claim 13 wherein said aqueous solution is acidified with acetic acid or glutamic acid.

23. A solution according to claim 13 wherein said surfactant is non-ionic.

24. A charge transfer complex according to claim 15 wherein said aqueous solution is acidified with acetic acid or glutamic acid.

25. A composition having disinfectant and cicatrizing activity, comprising a charge transfer complex of iodine with chitosan or a derivative thereof according to claim 5, at least one pharmaceutical or cosmetic excipient, and at least one surfactant.

* * * * *